United States Patent
Typpö et al.

(10) Patent No.: US 7,151,380 B2
(45) Date of Patent: Dec. 19, 2006

(54) MICROWAVE WATER WEIGHT SENSOR AND PROCESS

(75) Inventors: Pekka Typpö, Cupertino, CA (US);
Rudolf Münch, Koenigsbronn (DE);
Thomas Ischdonat, Bachhagel (DE);
Oliver Kaufmann, Heidenheim (DE)

(73) Assignee: Voith Paper Patent GmbH, Heidenheim (DE)

( * ) Notice: Subject to any disclaimer, the term of this patent is extended or adjusted under 35 U.S.C. 154(b) by 0 days.

(21) Appl. No.: 10/912,213

(22) Filed: Aug. 6, 2004

(65) Prior Publication Data
US 2006/0028213 A1    Feb. 9, 2006

(51) Int. Cl.
*G01R 27/32* (2006.01)
*G01G 9/00* (2006.01)

(52) U.S. Cl. .................. 324/643; 324/634; 73/865

(58) Field of Classification Search ................ 324/643, 324/544, 634
See application file for complete search history.

(56) References Cited

U.S. PATENT DOCUMENTS

| | | | |
|---|---|---|---|
| 3,079,551 A * | 2/1963 | Walker | 324/632 |
| 3,255,408 A | 6/1966 | Walker | |
| 3,442,756 A | 5/1969 | Lehtinen | 162/192 |
| 3,534,260 A * | 10/1970 | Walker | 324/640 |
| 3,815,019 A | 6/1974 | Wiles | |
| 4,037,462 A | 7/1977 | Necker et al. | |
| 4,104,584 A | 8/1978 | Miyai et al. | |
| 4,203,067 A * | 5/1980 | Fitzky et al. | 324/632 |
| 4,297,874 A * | 11/1981 | Sasaki | 73/73 |
| 4,484,133 A | 11/1984 | Riggin et al. | |
| 4,789,431 A | 12/1988 | Typpo | 162/263 |
| 5,086,279 A * | 2/1992 | Wochnowski et al. | 324/637 |
| 5,313,167 A * | 5/1994 | Marshall | 324/632 |
| 5,315,258 A * | 5/1994 | Jakkula et al. | 324/640 |
| 5,397,993 A * | 3/1995 | Tews et al. | 324/634 |
| 5,826,458 A | 10/1998 | Little | |
| 6,204,670 B1 * | 3/2001 | Joshi | 324/643 |
| 6,837,122 B1 * | 1/2005 | Herrmann et al. | 73/865 |
| 2004/0240512 A1 * | 12/2004 | Pesach | 374/43 |

FOREIGN PATENT DOCUMENTS

| | | |
|---|---|---|
| DE | 3339602 | 5/1984 |
| DE | 4000925 | 7/1990 |
| EP | 0541218 | 5/1993 |
| EP | 0558759 | 9/1993 |
| EP | 0903657 | 4/2002 |
| EP | 1342843 | 9/2003 |
| GB | 2297846 | 8/1996 |
| WO | 99/02979 | 1/1999 |
| WO | 00/09994 | 2/2000 |

OTHER PUBLICATIONS

Merriam-Webster's Collegiate Dictionary (Tenth Edition) (p. 1157, lines 43-44).*

(Continued)

*Primary Examiner*—Anjan Deb
(74) *Attorney, Agent, or Firm*—Greenblum & Bernstein, P.L.C.

(57) ABSTRACT

Sensor and process for measuring mass of water on a sheet forming fabric. The sensor includes a microwave element positionable to couple an electromagnetic field into a stock layer to be measured, and a microwave signal generator coupled to the microwave element to generate, in the microwave element, a microwave signal having a frequency lower than a relaxation frequency of water. The instant abstract is neither intended to define the invention disclosed in this specification nor intended to limit the scope of the invention in any way.

41 Claims, 9 Drawing Sheets

OTHER PUBLICATIONS

"Industrial Microwave Sensors", from Industrial Microwave Sensors XP002334964, by Ebbe Nyfors and Pertti Vainikainen, 1989.

"Microwave Microstrip Ring Resonator as a Paper Moisture Sensor: Study with Different Grammage", from Measurement Scien and Technology, IOP, Bristol, GB, vol. 13, No. 10, Oct. 2002, pp. 1558-1562, XP001201600, by R.A. Yogi et al.

"Frequency dependence of microwave moisture measurements of paper", from Journal of Microwave Power Canada, Mar. 1977, pp. 47-49, XP009069338, ISSN: 0022-2739; by F.Y. Chul et al.

"Microwave Moisture Meters for the Paper and Pulp Industry", from Measurement and Control, Institute of Measurement and Control, London, Great Britain, vol. 3, No. 3, Mar. 1970, pp. T33-T38, XP009063692, ISSN: 0020-2940; by K. Lindberg et al.

"Design Aspects of Stripline Resonator Sensors for Industrial Applications", from Journal Microwave Power Electromagnectic Energy, 1995, International Microwave Power Institute, Clifton, VA, USA, vol. 30, No. 4, 1995, pp. 246-257, XP009069104 by M. Fisher et al.

"Microwave Sensor System for the Consistency Measurement in the Pulp and Paper Industry", Sensors Update, Special Volume: RF and Microwave Sensing of Moist Materials, Food and Other Dielectrics, vol. 7, 2000, pp. 211-232, XP002390236, Weinhem, by P. Jakkula et al.

"Chapter 4, Forest Industry", Opportunities for Advanced Ceramics to Meet the Needs of the Industries of the Future, [Online] Dec. 1998, pp. 4-1-14-15, XP002390327. Retrieved from the Internet: URL:http://www.ms.ornl.gov/programs/energy/eff/cfcc/iof/chap4.pdf>; by D. Freitag et al.

\* cited by examiner

Figure 2
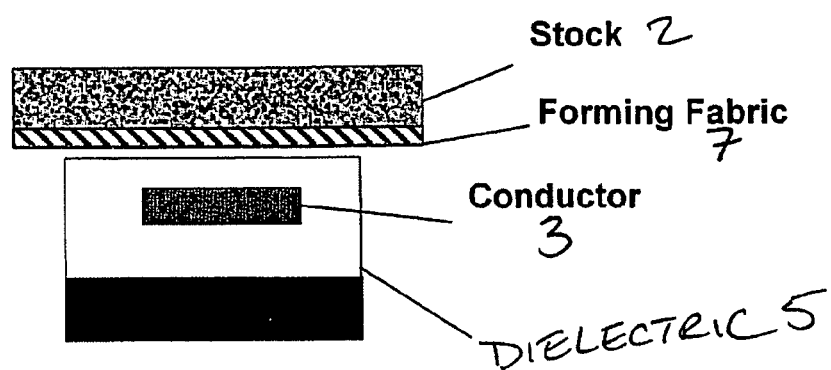
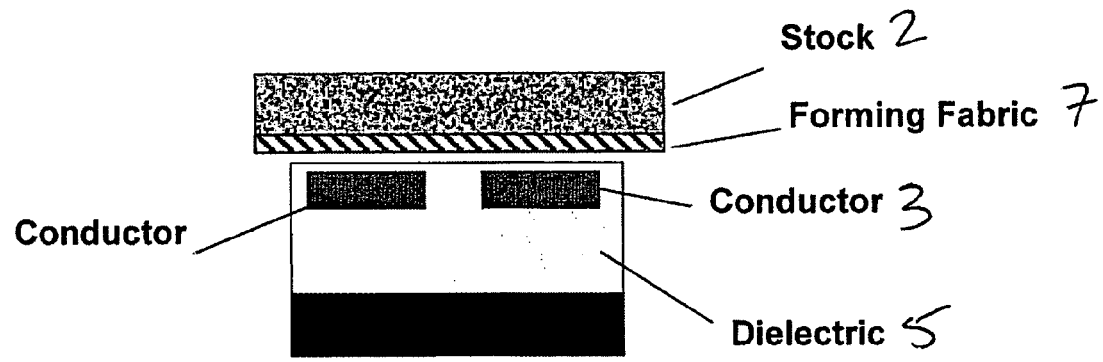
Figure 3

MICROWAVE WATER WEIGHT SENSOR AND PROCESS

FIELD OF THE INVENTION

The present invention is directed to a sensor and process for measuring water weight in the forming section of a paper making machine using microwaves.

DISCUSSION OF BACKGROUND INFORMATION

Various devices are known for determining the water weight in the forming section. However, these device are limited in that the water weight is indirectly determined, i.e., calculated from the measurement of another parameter. One such device (Honeywell SpectraFoil) calculates the water weight based upon a measurement of the conductance of the stock layer on the former. This device measures the electric current through the stock and is sensitive to chemical changes in the stock.

Another method described in U.S. Pat. Nos. 3,442,756 and 4,789,431 provides an ultrasonic measurement of the stock layer thickness by measuring reflectance of the ultrasonic sound from the top and bottom surface of the stock. Thus, this device provides essentially a "layer-thickness-measurement," however, it cannot be used after the dry line.

Another device provides a gamma backscatter based total mass measurement. However, this device is disadvantageous in that measurement noise is high and that the measurement requires the use of radioactive material.

In contrast to the foregoing devices, a single sided resonant microwave cavity sensor (ScanPro by Lorentzen & Wettre) is known, which more or less directly measures water weight. However, the size of these devices do not match the space requirements for paper making installations.

A further measurement method, which uses microwaves for measuring water weight in the forming section of the paper machine, has been described in detail in European Patent Application No. EP 0 903 657. While the described method uses a sensor that measures the moisture content (water weight) through the sheet supporting fabric, none of the commercially available microwave sensors are suited for this application, i.e., as noted above, the sensors such as the ScanPro do not match the space requirements.

Other commercially available microwave sensors, which are even smaller than the above-discussed ScanPro, are only able to sense a very thin layer of water above the sensor surface. Thus, these sensors are not suited for measuring water through the forming fabric.

Another microwave moisture content and weight of sheet device is known from U.S. Pat. No. 4,297,874, which utilizes a resonant cavity. In this device, the sheet passes through the resonant cavity to monitor attenuation or phase shift. However, like the other noted devices, the resonant cavity is too large for satisfactory use in the forming section.

SUMMARY OF THE INVENTION

The present invention provides a microwave sensor that overcomes the above-noted drawbacks of the prior art.

The sensor creates a microwave field that is partially in the material to be measured. This field is generated with a stripline or slotline microwave transmission line embedded into a ceramic foil, or with a transmitter antenna and a receiver antenna that coupled the microwave filed through the material. The dielectric constant of the materials around the transmission lines or in the space between the transmitter and receiver antennae influences the wave propagation velocity. The measurement is based either on propagation delay or by the phase. A stripline resonator can also be used. The resonator will essentially measure the wave propagation velocity in the resonant structure. The operating frequency is chosen to be significantly below the relaxation frequency of water around 22 GHz. The preferred operating frequency is between 1 GHz and 3 GHz, but other frequencies are possible.

Thus, in accordance with the invention, the water weight sensor can be install either on or inside a ceramic foil.

The sensor according to the instant invention is small enough to mount in a ceramic water removal element (foil). In this regard, neither the ScanPro nor any other commercially available microwave sensors, which are even smaller than the ScanPro, are small enough for mounting in a ceramic foil. Moreover, by building or placing the sensor into one or more of water foils, which are in contact with the fabric, there will be no variation in the distance between the sensing element and the sheet.

According to the invention, a sensor is provided that measures the water weight in the paper machine forming section. In particular, the sensor can be utilized before and as well after the dry line, can be used in double wire forming sections, and is dimensioned to be installed inside a ceramic foil.

Moreover, while the instant sensor is small enough to be installed inside a ceramic foil, the sensor should be powerful enough that the signal is able to penetrate a layer of ceramic in the foil and pass through the forming fabric into the stock layer. In this manner, single sided measurement is possible. Further, the present invention provides a cost effective sensor element that allows cost effective multi-sensor configurations to measure water weight simultaneously at various cross-machine direction positions, i.e., to produce a non-scanning measurement profile. Additionally, multiple sensors can be arranged to build an array in the cross-machine and/or machine direction. Machine direction arrays can be advantageous in determining the drainage profile.

The sensor according to the invention can be formed as a stripline or slotline microwave transmission line (planar waveguide) in order to create a microwave field. This microwave transmission line can be embedded into a ceramic foil. In this regard, the dielectric constant of the materials around the transmission lines influence the wave propagation velocity in the transmission line. Thus, the measurement can be based on either measuring the propagation delay in the transmission line or measuring the phase shift in the transmission line.

Alternatively, the sensor can be formed as a straight-line or ring resonator (planar resonator) in order to measure the wave propagation velocity in the resonant structure.

The operating frequency for the sensor is chosen to be below the relaxation frequency of water, which is around 22 GHz. Preferably, the operating frequency is 2.45 GHz, which permits the use of widely available integrated circuits originally designed for wireless communication applications. Of course, other frequencies are possible within the scope of the invention.

The present invention utilizes the fact that the dielectric constant of the stock in the forming section is primarily influenced by water, which has a high relative dielectric constant, approximately 80 in room temperature at frequencies up to several GHz. In this regard, the effect of the water weight on the microwave field applied to the sensor is measured by detecting, depending upon the sensor structure, either a change in propagation velocity or phase shift (for planar transmission line sensors) or a change in resonant frequency (for planar resonators). Further, increasing temperature will decrease the relative dielectric constant, so temperature measurement and temperature compensation is necessary in many cases.

This method can be used to build detector arrays both in cross machine and machine directions. Machine direction arrays can be used to determine the drainage profile.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 2 illustrates the sensor as a stripline transmission line;

FIG. 3 illustrates the sensor as a slotline transmission line;

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
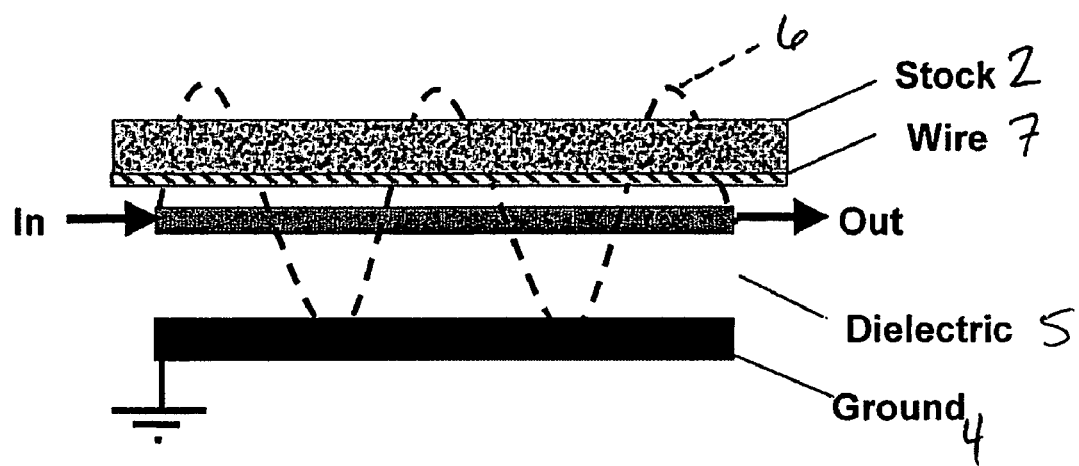
FIG. 1 illustrates an exemplary embodiment of the invention.

FIG. 1 illustrates a sensor 1 in accordance with the features of the present invention. In particular, sensor 1 can be positioned adjacent the sheet or web 2 supported on a forming fabric (plastic wire) 7 in a sheet forming section, where sheet 2 is almost all water. Sensor 1, which is a microwave element, includes a conductor 3 and a ground reference 4 separated by a dielectric layer 5. In this regard, sensor 1 can be formed by any microwave transmission line that will transmit an electromagnetic field that extends into sheet 2.

Sensor 1 is dimensioned so that it can be built into a ceramic water removal element (foil). In particular, the sensor is dimensioned, e.g., such that the long dimension is chosen to be similar the wavelength of the microwaves, typically between 50 mm and 125 mm (but other dimensions are possible). As an alternative, sensor 1 can be arranged to directly or indirectly through a guide surface (not shown) contact the forming fabric, e.g., a plastic wire. In such an arrangement is it advantageous to position sensor 1 between dewatering elements. Thus, whether housed in the ceramic foil or arranged to contact the forming fabric, the sensor is maintains a constant gap from the forming sheet. The sensor can be mounted or installed into a cavity machined into a foil. In this regard, the cavity can be machined on the backside of the foil with a layer of dielectric foil material left to cover the sensor and to provide a smooth surface, or the cavity can be machined on the front side of the foil and covered with a smooth layer of dielectric material. It is also possible to have a conductive transmission line or antenna material on the surface of the foil. In this instance, the conductive material must be chosen to have similar wear properties as the foil itself in order to avoid an uneven surface arising after or as the foil or the electrode wears. With a ceramic foil, the electrodes can be made out of conductive ceramics, such as Silicon Carbide. Sensor 1 is a microwave element that couples a microwave field 6 into sheet 2. In particular, the frequency field is selected to have a frequency lower than the relaxation frequency of water, i.e., less than 22 GHz, and preferably 2.45 GHz, because, at frequencies up to several GHz, the dielectric constant for water is approximately 80 at room temperature. Therefore, within the desired frequency range, the dielectric constant of the stock is primarily influenced by the water. Moreover, the above-noted preferred operating frequency allows the use of commercially available integrated circuits designed for wireless communication.

It is noted that the transmission of microwaves varies according to the dielectric constant of the material through which they are passing. Thus, in the exemplary embodiment of the invention, the effect of the mass of water or water weight on the microwave field is measured, e.g., change in wave propagation velocity or phase shift, or change in resonant frequency. Propagation velocity is inversely proportional to the square root of the effective dielectric constant of the media in which the wave travels. Effective dielectric coefficient depend on the local dielectric constants inside the microwave field, and it is highly dependent on the measurement geometry, so the sensor calibration algorithm will vary a great deal depending on the geometry. Propagation velocity can be measured by measuring the delay directly, by measuring a signal phase shift, or by measuring the resonant frequency of an element placed close to the sheet.

Delay can be measured by using a well-known frequency modulated continuous wave method, or by using the sensing element as the delay element in a delay line oscillator. Once delay in the sensing element is determined, propagation velocity v can be calculated:

i $v = L/t$, where:

L is the length of the sensing element t is the delay through the sensing element In case of a resonant element the relationship between the resonant length L, frequency f, and propagation velocity v is:

$$v = f*L/(\frac{1}{2}+n/2),$$

if both ends of the element are electrically open, or $$v = f*L/(\frac{1}{4}+n/2),$$

if one end of the element is electrically shorted and the other end open.

n=0, 1, 2, 3, . . . .

Normally the lowest resonance (n=0) is used, but higher resonances can also be chosen.

If phase shift is used, the velocity can be calculated from the measured phase shift using the following:

$$v = \{t0 + [\phi/(2*\pi*f)]\}/L,$$

where:

t0 is the fixed delay for the phase reference (LO) signal minus the fixed delay of the measurement (RF) signal outside the actual sensing area.

f is the frequency

L is the length of the transmission line $\phi$ is the phase shift

With the known propagation velocity the effective dielectric constant is:

$$\in_{eff} = 1/(\mu*v^2),$$

where:

$\mu$ is the permeability of the material (in the absence of ferromagnetic materials virtually constant)

The relationship between $\in_{eff}$ and the mass of water is complex, but since the volume of the sheet in the microwave field is small in most cases, and most of the microwave field energy is outside the sheet, the effect of water can be treated as a small perturbation. By differentiating the equation above way we get:

$$\Delta m = -2*[\in_{eff}/(d\in_{eff}/dm)]*(\Delta v/v0),$$

where:

$$\Delta m = m - m0$$

$$\Delta v = v - v0$$

m0 is a nominal water weight value v0 is the nominal propagation velocity corresponding to m0 m is the water weight

In this formula $-2*[\in_{eff}/(d\in_{eff}/dm)] = B$ can be treated as a calibration constant. Variable v0 can be measured when the forming wire is empty (m0=0) and stored as a sensor standardization value. This way the calculation formula becomes:

$$m = B*x,$$

where:

$$x = (v/v0 - 1)$$

This formula can then be corrected for non-linearity to allow a wider measuring range by adding polynomial correction terms:

$$m = A + B*x + C*x^2 + D*x^3,$$

where:

A, B, C, and D are calibration constants.

This calibration algorithm is just an example of a simple way to calculate water weight from the measured propagation velocity. Many other formulas can be used equally well.

Also, nominal propagation velocity v0 can be treated as a constant and it can be included in the calibration constants, in which case x=v−v0.

Sensor 1 illustrated in FIG. 1 generally depicts a microwave sensor in which the microwave field 6 penetrates the entire thickness of sheet 1. FIGS. 2 and 3, by way of example, illustrate specific planar waveguide arrangements utilized in accordance with the invention. As shown in FIG. 2, sensor 1 can be formed as a stripline transmission line 1.1, while, as shown in FIG. 3, sensor 1 can be formed as a slotline transmission line 1.2. As another alternative, sensor 1 can be formed as a dielectric waveguide. Dielectric wave guide uses a strip of dielectric material with either conductors on the sides to prevent energy from escaping, or by relaying on total internal reflection, in which case the surrounding material has a lower dielectric coefficient than dielectric material conducting microwave energy. Microwave energy on the surface in contact with the sheet would leak into the sheet, either because the evanescent field will extend outside the waveguide even when the conditions are right for total internal reflection, or because the waveguide design would be made intentionally leaky to increase the interaction with the sheet. This can be done by choosing the dielectric material so that the dielectric constant of the sheet is either close to or larger than the dielectric constant of the wave-guide. This principle can also be used without containing the microwave energy in a waveguide just by placing a transmitter and receiver antenna pair on dielectric material in contact with the sheet. This dielectric material can the ceramic foil used as a water-removing element.

Conductors used for both the antenna arrangements and the strip- and slotlines are thin metal foils on dielectric material. The dielectric material can be made out of a stable high frequency circuit board material (Duroid, Teflon, etc). It can also be a ceramic as long as the dielectric loss in the dielectric material is low. Aluminum Oxide is a suitable ceramic for this purpose. Metal conductors must in most cases be separated from the actual forming wire by a layer of continuous foil (water removal element) material. In some cases this material can be plastic, but typically it is made out of hard ceramic. With striplines and slotlines the microwave field doesn't extend very far outside the conductor, thus the distance between the transmission line and the forming fabric should be as small as possible without compromising the strength of the surface. In practice about 4–5 mm is as close as the strength requirement allows. With the antenna pair approach the field geometry is wider, and it is possible to operate with the coupling antennae on the sides of the ceramic foil, or even on the back of the foil. This way the antennae would typically be about 10–12 mm from the forming wire and placed about 50–100 from each other. Ceramic material must not only have a low dielectric loss at microwave frequencies, but also have a dielectric constant that is similar or less that the dielectric constant of the forming wire and the water it contains, or the stock on the wire. If the dielectric constant of the ceramic is significantly higher than the material on it, then most of the energy can be reflected back from the ceramic surface reducing the sensitivity of the sensor. Aluminum Oxide ceramic has a relative dielectric constant at 9.8, which is lower than the dielectric constant of stock and water filled forming wire, so Aluminum Oxide and similar ceramics are suitable for this purpose.

Please advise us the manner in which the stock temperature measurement (your claim 15) are used to correct water weight readings, and whether and how this correction relates to the inventive sensor. In other words, please advise whether the sensor reading is corrected prior to being manipulated/processed to calculate the water weight or whether the correction is performed as part of the manipulation/processing of data. In the latter case (as discussed above), the application should disclose the manner in which the data is manipulated/processed (and corrected) in order to calculate water weight.

Temperature correction will be applied as a part of the general water weight calculation. The dielectric coefficient of water drops with increasing temperature (relative dielectric coefficient is 80 at 20° C. and 50 at 100° C.). Wood fiber has a relative dielectric coefficient that is approximately 6 at room temperature and increases with increasing temperature. The net effect is that the dielectric coefficient of the paper stock that the measurement of water weight is based on will depend on both the temperature and the consistency of the stock. Typically fiber and water temperature coefficients cancel each other when the water content is about 30%. Since the water content in the forming section is always more than 80%, the dielectric coefficient of water will dominate. The correction required for compensating the dielectric coefficient for temperature is an almost linear function of temperature.

Temperature correction has been used for microwave moisture sensors for a long time. It was mentioned here for the sake of completeness.

Sensor response will initially be measured with and empty forming fabric and the result is stored and subtracted from sensor readings during actual measurement. The difference is corrected for temperature and consistency and the result is linearized with a polynomial linearization algorithm:

$$Mw = A + B*x + C*x^2 + D*x^3$$

Where:

$$x = (S - S0)*[1 + E*(\text{consistency}) + F*(T - T0)]$$

Coefficients A through F are calibration constants,
S is sensor output,
S0 is sensor output measured with an empty forming wire,
Consistency is calculated using data from dry end of the machine; small correction calculated using iteration,
T is stock temperature
T0 is nominal stock temperature.

Resonator designs shown in the drawings are conventional designs commonly used in microwave engineering for narrowband filters etc. They are planar designs with no structure in the vertical direction. However, it is noted that their use on a forming section foil to measure water weight is novel.

Figure 4:
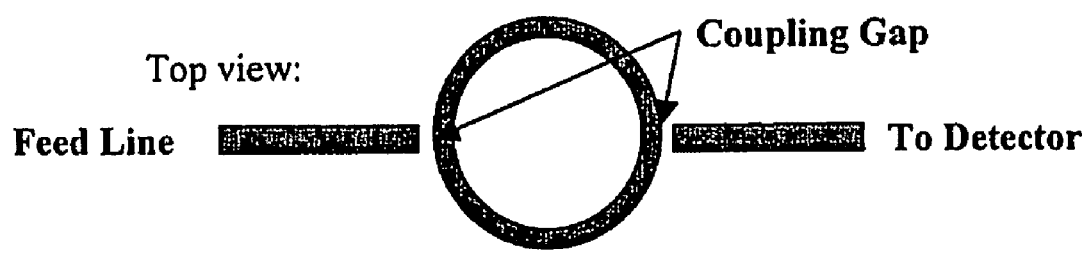
FIG. 4 illustrates the sensor as a ring resonator.
Figure 5:
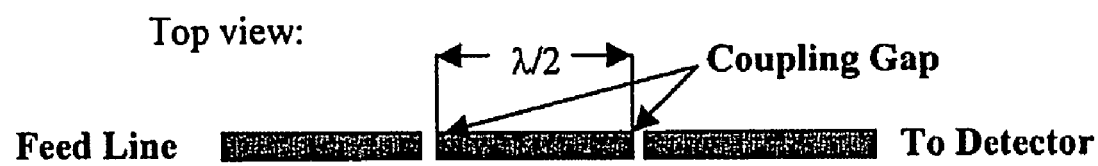
FIG. 5 illustrates the sensor as a straight-line resonator.

As an alternative, sensor 1 can be formed by a resonator coupled to sheet 2. FIGS. 4 and 5, by way of further example, illustrate planar gap resonator structures in accordance with the invention. As shown in FIG. 4, sensor 1 can be formed as a ring resonator 1.3, e.g., a planar ring resonator, while, as shown in FIG. 5, sensor 1 can be formed as a straight-line resonator. It is noted that the embodiments in FIGS. 4 and 5 are provided merely for exemplary purposes, and that other shapes and/or coupling methods can be utilized herein without departing from the scope of the invention. Further, other types of resonator can be used in accordance with the invention.

When sensor 1 is positioned in the desired location within the paper machine, i.e., in the forming section, the effect of the microwave field on sheet 2 is measured to calculate the water weight. In this regard, a number of parameters or effects of the microwave field can be measured, e.g., attenuation, phase shift, velocity.

Moreover, in the exemplary embodiment of the invention, sensor 1 is located on or as part of the ceramic foil in the forming section. In this regard, it is noted that the sensor can be formed on a ceramic layer applied onto the foil, such that the sensor is sandwiched between the ceramics. However, because the instant invention is detecting the dielectric influence of water on the microwave field, the thickness of the ceramic layer on which sensor 1 is formed should not be greater than 5 mm, The ceramic layer thickness of 5 mm maximum refers to a given width of a transmission line. With a 10 mm wide stripline the ceramic thickness of up to 5 mm can be tolerated if the ceramic is Aluminum oxide. Different ceramics and different transmission line widths result in different maximum thicknesses, and is preferably less than 4 mm. This is because the thicker the ceramic layer above sensor 1, the smaller the effect of the water on the microwave field. The reason this method can operate through a thicker ceramic layer is because then the microwave field is distributed uniformly through the thickness of the ceramic and the sheet, while with a strip- or slotline the field intensity drops rapidly as the distance from the conductor increases.

Further, a silicon carbide insert, preferably a thin layer of ceramic, could be provided on, and preferably laminated to, the front face of a foil. Moreover, a conductive pattern for sensor 1 can be provided behind this insert (layer). With this arrangement, the layer thickness can be 3 mm or less. The conductive patterns may be made with thin metal foils having suitable thermal expansion properties, or created with conductive ink sintered into the surface of the thin ceramic layer. Conductive pattern on the surface or behind a thin ceramic insert on the surface will not reduce the strength of the foil, so the protective layer can be very thin, or if the conductive material is similar to the ceramic itself, such as Silicon Carbide, a protective cover layer may not be required at all. The surface just has to be ground to provide a smooth finish.

Figure 10:
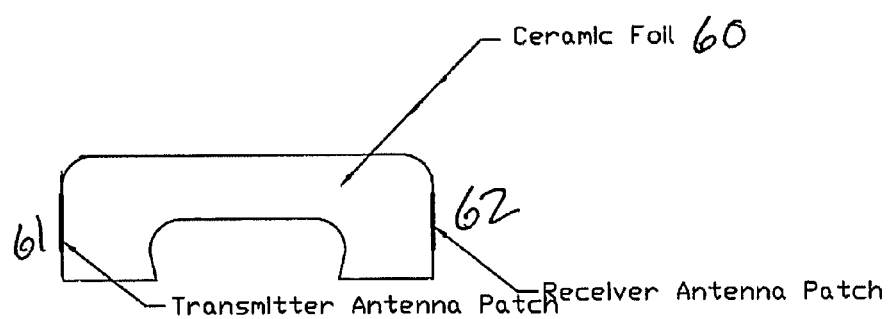
FIG. 10 illustrates a foil having separate transmitter and receiver patches.

In a further embodiment, as shown in FIG. 10, sensor 1, instead of modifying the foil, can be formed by two thin antenna patches 61 (transmitter) and 62 (receiver) attached to foil 60, one upstream and the other downstream relative to the web travel direction. These antenna patches are extremely thin, less than 1 mm and should have no effect on drainage. In an alternative, sensor 1 could be arranged to have a double pass system, in which transmitter 61 and receiver 62 are located on a same side of foil 60 and a thin conductive strip can be arranged on the opposite side of foil 60 to act as a reflector. These antenna patches can also be placed underneath the foil, in which case they do not interfere with water drainage from the sheet at all. Further, when sensor 1 is formed as a dielectric waveguide (not shown), the sensor can be formed into the foil material with conductive barriers outlining the appropriate waveguide shape. It is even be possible to use the foil material to conduct microwaves directly by just inserting transmitter and receiver electrodes into the dielectric foil material. In this arrangement, the wave propagation velocity would even be influenced by water on the forming wire. Moreover, while there may be a mismatched impedance, propagation velocity can still be measured. In this arrangement the wave propagation velocity is influenced by water on the forming wire. This is the same idea that was referred to above using the ceramic foil itself to conduct microwaves.

Figure 11:
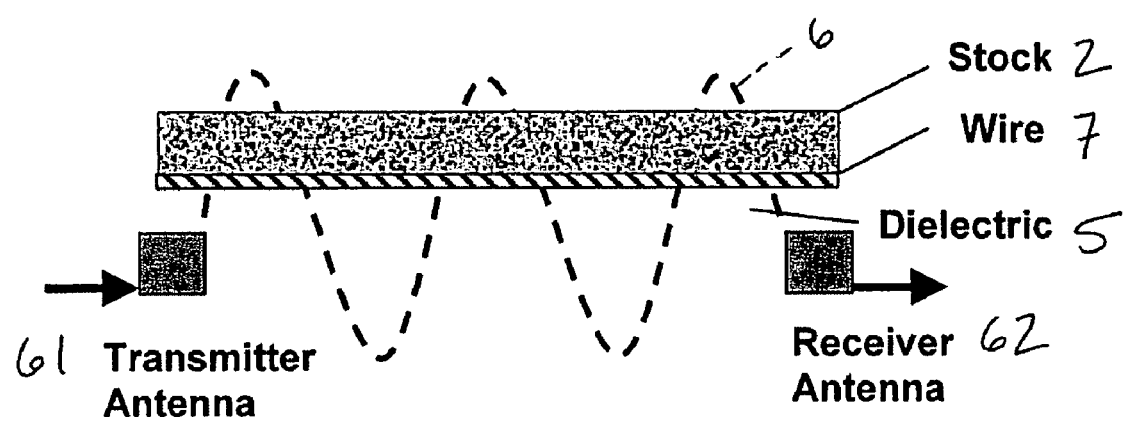
FIG. 11 illustrates the sensor with a transmitter antenna and a receiver antenna.

In a further embodiment, as shown in FIG. 11, sensor 1 can be formed with a transmission antenna 61 and a receiver antenna 62.

Figure 6:
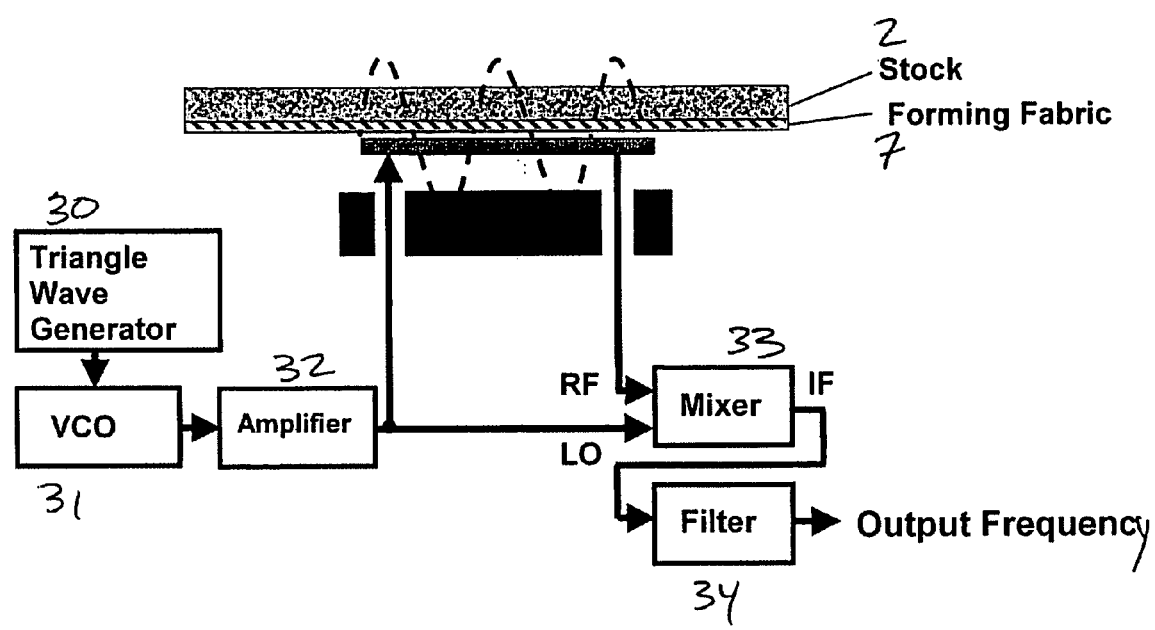
FIG. 6 illustrates a procedure for detecting propagation velocity of a signal.

As shown in FIG. 6, a frequency modulated continuation wave method can be employed to measure the effect of sheet 2 on the propagation velocity of the microwave signal through the transmission line. This method is generally used in short distance radar and microwave level detectors, and is performed by comparing a signal received at the target with a direct signal. In particular, a triangle wave generator 30 is coupled to a voltage controlled oscillator 31 in order to produce a signal having a frequency modulated with a triangle wave. The signal is amplified in amplifier 32 and then split to pass through sensor 1 and pass directly to mixer 33. The signal received from the target, i.e., influenced by sheet 2 is also coupled to mixer 33, so that the two signal can be compared. As the signal received from the target will be delayed slightly, the delayed signal will have a different frequency than that of the direct signal at mixer 33, so that the IF output of mixer 33 will be filtered in filter 34 and have a beat frequency proportional to the delay. From this determined delay, the mass of the water is determined by Assuming that the LO input to the mixer is adequate to fully turn the mixer on, the effect of the LO signal amplitude variation on the mixer output is small. The DC-output from a mixer used as a phase detector is in that case proportional to the amplitude of the RF input signal times the cosine of the phase angle between the LO and RF signals. Thus the phase angle is:

$$\phi = \arccos(V_{IF}/V_{RF}),$$

where:

$V_{IF}$ is the signal from the mixer IF output $V_{RF}$ is the RF signal amplitude The phase angle is used to determine signal propagation velocity, and the velocity is used to determine water weight. Phase difference $\phi$ between the LO and RF inputs relates to the propagation velocity in the following way:

$$v = \{t0 + [\phi/(2*\pi*f)]\}/L,$$

where:

t0 is the fixed delay for the LO signal minus the fixed delay of the RF signal outside the actual sensing area.

f is the frequency

L is the length of the transmission line

With regard to the foregoing discussion, it is noted that the signal received from the target is a signal that passes through a transmission line having a variable delay, which depends upon the basis weight of sheet 2. The foregoing discussion of measuring velocity is merely exemplary and should not be construed as limiting. It is noted that any procedures for determining velocity can be utilized without departing from the spirit of the invention. Further, in order to minimize the effect of reflections on the propagation velocity measurement, the ends of the transmission lines can be rounded or tapered.

Figure 7:
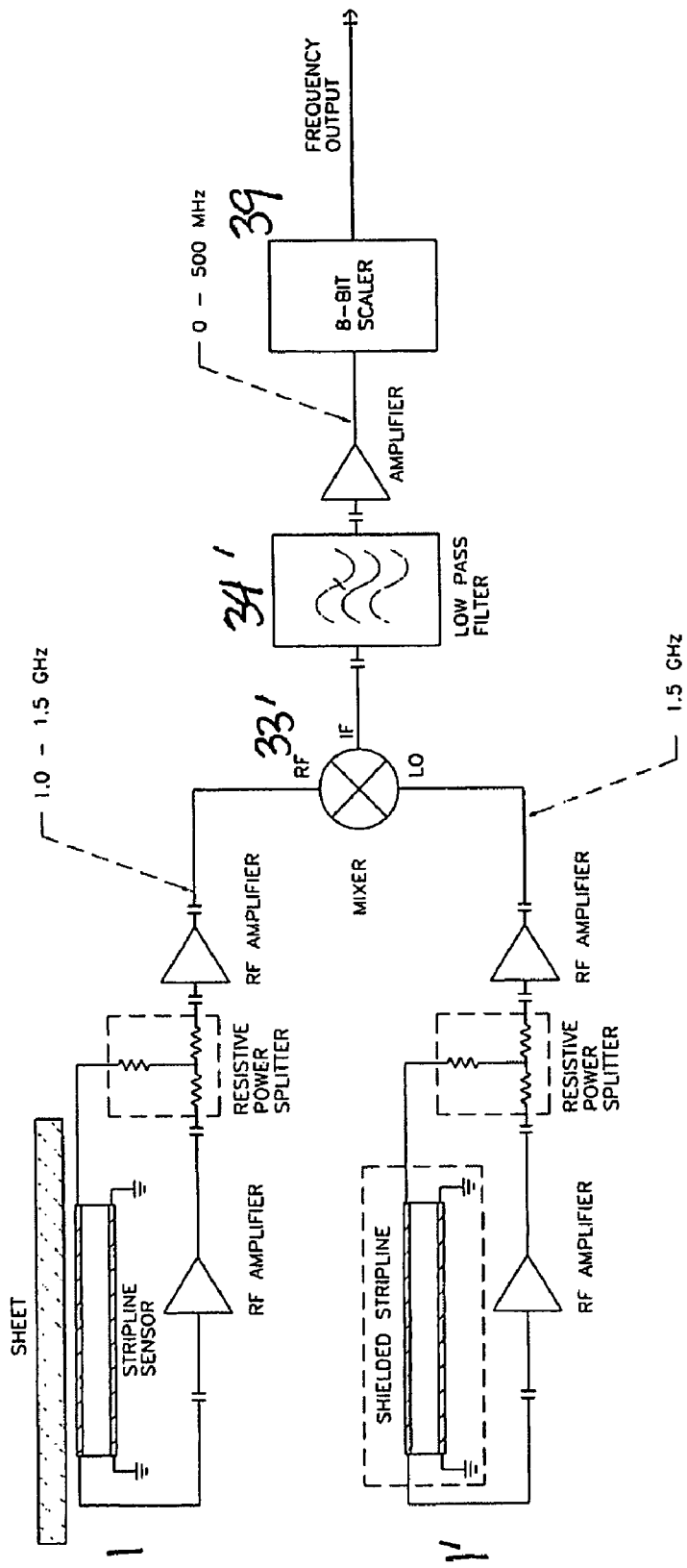
FIG. 7 illustrates an alternative procedure for detecting propagation velocity of the signal.

Another device for measuring propagation velocity is shown in FIG. 7. This device includes two delay line oscillators, one connected to the sensor stripline 1 and the other connected to a shielded reference stripline 1'. Like the device shown in FIG. 6, input signals LO and RF of mixer 33' are compared so that the sensor signal is taken from output signal IF via amplifier/filter 34' and a frequency scaler 39. Again, from this determined delay, the mass of the water is determined by Propagation velocity is inversely proportional to the square root of the effective dielectric constant of the media in which the wave travels. Effective dielectric coefficient depend on the local dielectric constants inside the microwave field, and it is highly dependent on the measurement geometry, so the sensor calibration algorithm will vary a great deal depending on the geometry. Propagation velocity can be measured by measuring the delay directly, by measuring a signal phase shift, or by measuring the resonant frequency of an element placed close to the sheet. Delay is monitored in the manner discussed above.

Figure 8:
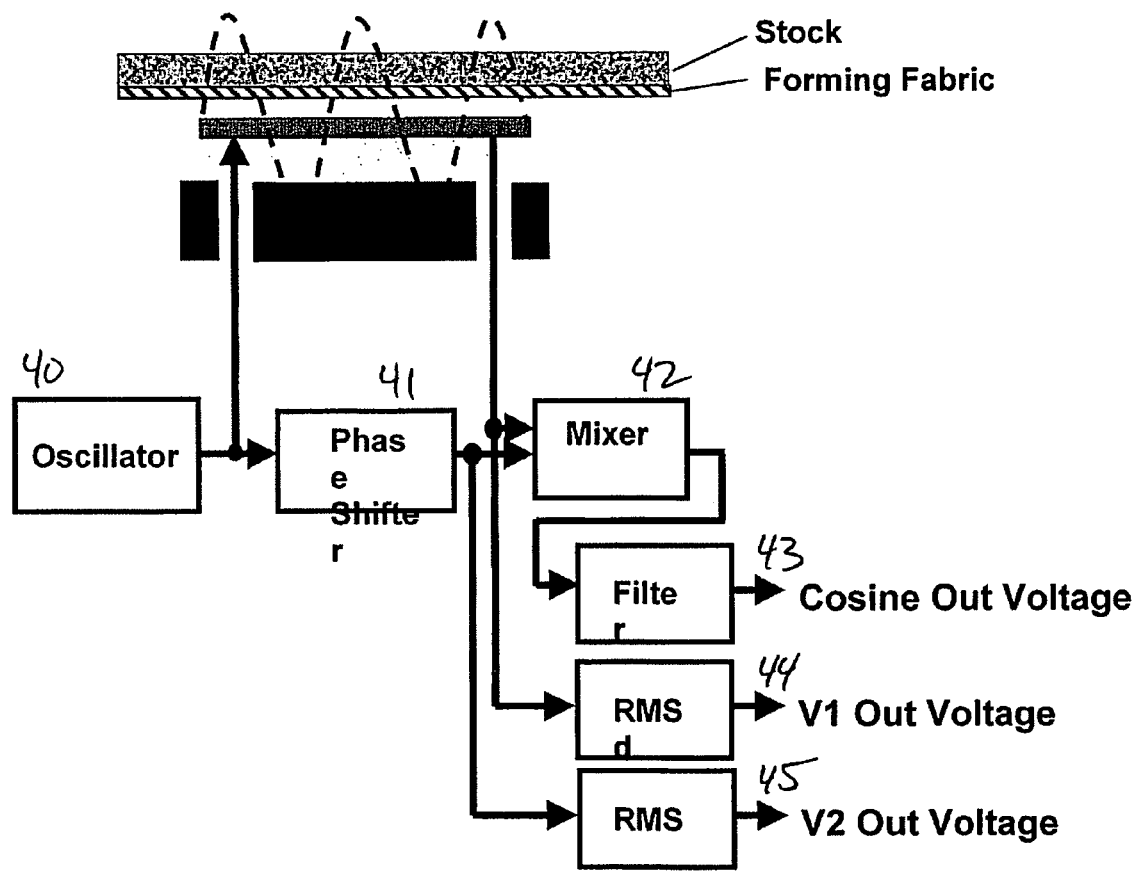
FIG. 8 illustrates a procedure for detecting phase shift of a signal.

The frequency modulated continuation wave method finds utility with the planar waveguide microwave elements, as depicted in FIGS. 1–3. Alternatively, water weight can be calculated from a measurement of phase shift of the microwave signal directed through sheet 2. As shown in FIG. 8, a microwave signal from oscillator 40 is split and coupled to sensor 1 and to phase shifter 41, and a mixer 42, e.g., a dc-coupled mixer, is arranged to receive the signal LO from phase shifter 41 and the signal RF from output of sensor 1. The signal from mixer 42, which is filtered by filter 43, outputs a signal proportional to the amplitudes of input signals LO and RF and the cosine of the phase angle between input signals LO and RF, which have a same frequency. Moreover, signals LO and RF are coupled to respective voltage detectors 44 and 45, e.g., RMS detectors, to measure the voltage amplitudes of signals LO and RF. In this regard, in order for mixer 42 to be used as a perfect phase detector, the measured amplitudes of signals LO and RF should be included in the calculation of phase angle. Moreover, the above-discussed procedure for measuring phase shift is provide by way of example, and should not be construed as limiting. In fact, it is noted that any procedures for determining phase shift can be utilized without departing from the spirit of the invention. From this determined phase shift, the water weight is determined by Assuming that the LO input to the mixer is adequate to fully turn the mixer on, the effect of the LO signal amplitude variation on the mixer output is small. The DC-output from a mixer used as a phase detector is in that case proportional to the amplitude of the RF input signal times the cosine of the phase angle between the LO and RF signals. Thus the phase angle is determined in the manner discussed above.

In another advantageous measuring procedure, the measurement can be performed using a wide range of frequencies to determine a spectrum, e.g., propagation velocity or signal phase shift; dispersion, and the amount of water can be calculated from variations in the spectrum. The range of frequencies would include higher frequencies where the dielectric constant starts to drop as the frequency approaches the 22 GHz water molecule relaxation. This drop depends on temperature and to some degree conductivity. Measuring the drop at higher frequencies and comparing these measurement to the data at lower frequencies facilitates a very accurate temperature compensation based on the signal ratios at high vs. low frequencies.

Figure 9:
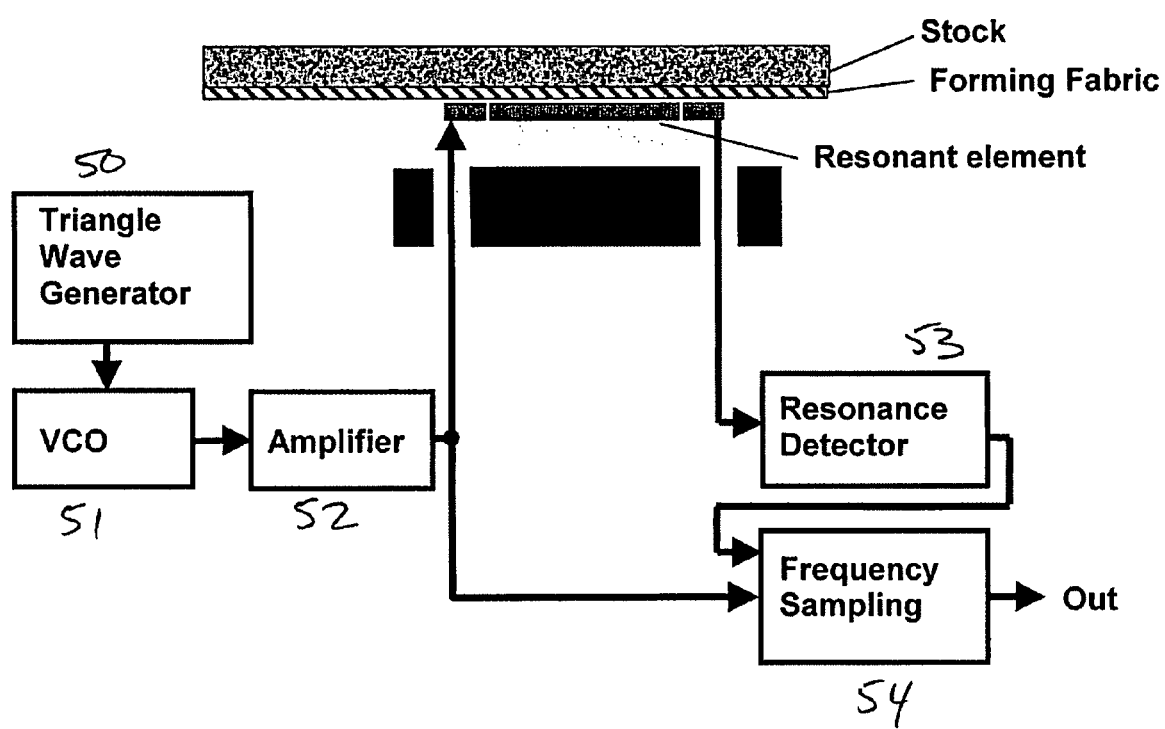
FIG. 9 illustrates a procedure for detecting resonant frequency of a resonator.

When sensor 1 is formed as a resonator, the resonating frequency of the resonator is measured and used to calculate the basis weight of sheet 2. While there are many ways to detect the resonant frequency of a resonator, an exemplary procedure is illustrated in FIG. 9. However, it is noted that this procedure is not intended as limiting and that any procedures for determining resonant frequency can be utilized without departing from the spirit of the invention. A beneficial method is shown below. In the exemplary embodiment, a triangle wave is generated by triangular wave generator 1, and the frequency of a voltage controlled oscillator (VCO) 50 is scanned up and down over a range where resonance is to be expected. At resonance, the power from resonance detector 53 reaches a maximum, and the frequency of oscillator 50 is tracked and sampled by frequency sampling unit 54 when the derivative of the power reaches zero at a predetermined minimum power level. From this detected resonance, the water weight is determined in the manner set forth above.

According to the present invention, detector arrays can be formed of a number of sensors 1 in order to facilitate cross machine direction and/or machine direction measurements of water weight profile. Further, machine direction arrays can be used to determine the drainage profile in the forming section. Alternatively or additionally, the instant sensors can be used with conventional scanning applications. Still further, additional measurements, such as temperature of the stock, can be taken and used to correct water weight readings. Sensor response will initially be measured with and empty forming fabric and the result is stored and subtracted from sensor readings during actual measurement. The difference can be corrected for temperature and consistency by including a multiplicative correction as shown below:

$$m = A + B^*x + C^*x^2 + D^*x^3$$

where:

$$x = (v/v0 - 1)^*[1 + E^*(\text{consistency}) + F^*(T - T0)]$$

Coefficients A through F are calibration constants,
S is sensor output,
S0 is sensor output measured with an empty forming wire,
Consistency is calculated using data from dry end of the machine; small correction calculated using iteration,
T is stock temperature
T0 is nominal stock temperature.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A sensor for measuring mass of water on a sheet forming fabric, comprising:
   a microwave element positionable in a forming section to couple an electromagnetic field into a stock layer to be measured; and
   a microwave signal generator coupled to said microwave element to generate, in said microwave element, a microwave signal having a frequency lower than a relaxation frequency of water,
   wherein the frequency lower than the relaxation frequency of water is a frequency between 2.4 GHz and 2.5 GHz.

2. The sensor in accordance with claim 1, further comprising a mounting device for mounting said microwave element a predetermined distance from the sheet.

3. The sensor in accordance with claim 1, wherein a microwave field generated in said microwave element is effected by the mass of water.

4. The sensor in accordance with claim 3, wherein the effect of the stock layer on the microwave field is used to calculate the water mass.

5. The sensor in accordance with claim 3, wherein the effect of the stock layer on the microwave field includes one of propagation velocity, phase shift, attenuation, or resonant frequency.

6. The sensor in accordance with claim 1, wherein the frequency lower than the relaxation frequency of water is lower than 22 GHz.

7. The sensor in accordance with claim 1, wherein the frequency lower than the relaxation frequency of water is a frequency at which the dielectric constant of water is about 80.

8. The sensor in accordance with claim 1, wherein said microwave element comprises one of a transmitter-receiver antenna pair, a resonant element, and a waveguide.

9. The sensor in accordance with claim 1, wherein said microwave element comprises a stripline transmission line.

10. The sensor in accordance with claim 9, wherein ends of said transmission line are one of tapered or rounded.

11. The sensor in accordance with claim 1, wherein said microwave element comprises a transmission line.

12. The sensor in accordance with claim 11, wherein said transmission line comprises a stripline transmission line.

13. The sensor in accordance with claim 11, wherein said transmission line comprises a slotline transmission line.

14. The sensor in accordance with claim 11, wherein said transmission line comprises a dielectric waveguide.

15. The sensor in accordance with claim 11, further comprising a device for measuring microwave signal propagation velocity through said transmission line, wherein the water mass is calculated from the measured velocity.

16. The sensor in accordance with claim 15, wherein the microwave signal propagation velocity is measured using a Frequency Modulated Continuous Wave method.

17. The sensor in accordance with claim 11, further comprising a device for measuring microwave signal phase shift through said transmission line, wherein the mass of the water is calculated from the measured phase shift.

18. The sensor in accordance with claim 17, further comprising a dc-coupled mixer structured and arranged to measure the microwave signal phase shift.

19. The sensor in accordance with claim 11, further comprising a device for measuring the effect of the microwave field in the transmission line, in which said device uses a wide range of frequencies to determine a spectrum, wherein the mass of the water is calculated from variations in the spectrum to identify specific components in the sheet.

20. The sensor in accordance with claim 1, wherein said microwave element is formed onto a ceramic foil.

21. The sensor in accordance with claim 1, wherein said microwave element is formed within a ceramic foil.

22. The sensor in accordance with claim 1, wherein said microwave element is formed on a layer attachable to a water removal element.

23. The sensor in accordance with claim 22, wherein said layer is a ceramic layer laminated onto a surface of said water removal element.

24. The sensor in accordance with claim 23, wherein said microwave element comprises a conductive pattern sintered onto said layer.

25. The sensor in accordance with claim 1, wherein the microwave field is coupled to the stock layer on a forming fabric.

26. The sensor in accordance with claim 1, wherein said microwave element comprises a microwave resonator.

27. The sensor in accordance with claim 26, wherein the stock layer is carried through the microwave field on a forming fabric.

28. The sensor in accordance with claim 26, further comprising a device for measuring a resonant frequency, wherein the measured resonant frequency is used to calculate the mass of the water.

29. The sensor in accordance with claim 26, wherein said microwave resonator comprises a planar resonator.

30. The sensor in accordance with claim 26, wherein said planar resonator comprises a ring resonator.

31. The sensor in accordance with claim 26, wherein said planar resonator comprises a straight-line resonator.

32. The sensor in accordance with claim 26, wherein said planar resonator comprises a planar gap coupled resonator.

33. The sensor in accordance with claim 26, wherein said microwave element is formed one of in and on a ceramic foil.

34. The sensor in accordance with claim 1, wherein a plurality of microwave elements are arranged in an array.

35. The sensor in accordance with claim 34, wherein said array is arranged in a machine direction.

36. The sensor in accordance with claim 34, wherein said array is arranged in a cross-machine direction.

37. The sensor in accordance with claim 1, wherein a plurality of microwave elements are built one of into and onto a ceramic foil.

38. The sensor in accordance with claim 1, further comprising a stock temperature sensor, wherein a temperature reading from said temperature sensor is used to correct water weight readings.

39. The sensor in accordance with claim 1, wherein said sensor is located between dewatering elements and at a defined distance to a forming fabric supporting the stock layer.

40. The sensor in accordance with claim 1, wherein said microwave generator is structured to generate multiple microwave frequencies one of simultaneously or sequentially.

41. A process of monitoring a stock layer in a production line, comprising:

penetrating the stock layer in a forming section with microwaves having a frequency less than a relaxation frequency of water; and measuring an effect of the stock layer on the microwaves wherein the frequency less than the relaxation frequency of water is a frequency between 2.4 GHz and 2.5 GHz.

* * * * *